(12) United States Patent
Leight et al.

(10) Patent No.: US 9,072,805 B1
(45) Date of Patent: Jul. 7, 2015

(54) PORTABLE DECONTAMINATION UNIT

(71) Applicant: AMERICAN STERILIZER COMPANY, Mentor, OH (US)

(72) Inventors: Steven D. Leight, Brunswick, OH (US); Cameron J. Pedersen, Painsville, OH (US); Francis J. Zelina, Lake City, PA (US)

(73) Assignee: AMERICAN STERILIZER COMPANY, Mentor, OH (US)

( * ) Notice: Subject to any disclaimer, the term of this patent is extended or adjusted under 35 U.S.C. 154(b) by 0 days.

(21) Appl. No.: 14/572,985

(22) Filed: Dec. 17, 2014

Related U.S. Application Data

(60) Provisional application No. 61/921,586, filed on Dec. 30, 2013.

(51) Int. Cl.
*A61L 2/24* (2006.01)
*A61L 2/20* (2006.01)

(52) U.S. Cl.
CPC .. *A61L 2/208* (2013.01); *A61L 2/24* (2013.01)

(58) Field of Classification Search
CPC .................................. A61L 2/208; A61L 2/24
USPC ........................................................ 422/292
See application file for complete search history.

(56) References Cited

U.S. PATENT DOCUMENTS

| 7,431,900 | B2 | 10/2008 | Hill et al. ...................... 422/305 |
| 7,700,056 | B2 | 4/2010 | Hill et al. ...................... 422/292 |
| 8,409,501 | B2 | 4/2013 | McDonnell et al. ............ 422/28 |
| 2007/0098592 | A1 | 5/2007 | Buczynski et al. ............... 422/3 |
| 2010/0143204 | A1 | 6/2010 | Ortiz et al. ..................... 422/119 |
| 2013/0078153 | A1 | 3/2013 | Hill et al. ...................... 422/111 |

*Primary Examiner* — Sean E Conley
(74) *Attorney, Agent, or Firm* — Kusner & Jaffe; Michael A. Centanni

(57) ABSTRACT

An apparatus for decontaminating a region within an enclosure. The apparatus comprises a conduit having a passageway therethrough that defines a path for a carrier gas. A plurality of tube sections, each of the tube sections having an opening extending therethrough, is selectively movable into and out of a gap in the conduit. A heating element is disposed in one of the tube sections and is operable to heat the carrier gas flowing therethrough. A destroyer is disposed in another of the tube sections and is operable to destroy sterilant in the carrier gas. A controller controls movement of the tube sections into and out of the gap.

20 Claims, 11 Drawing Sheets

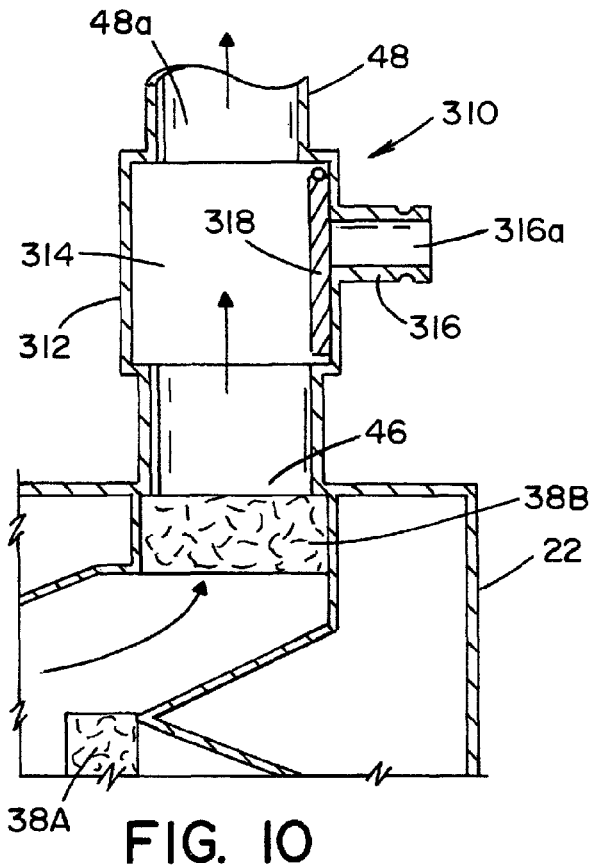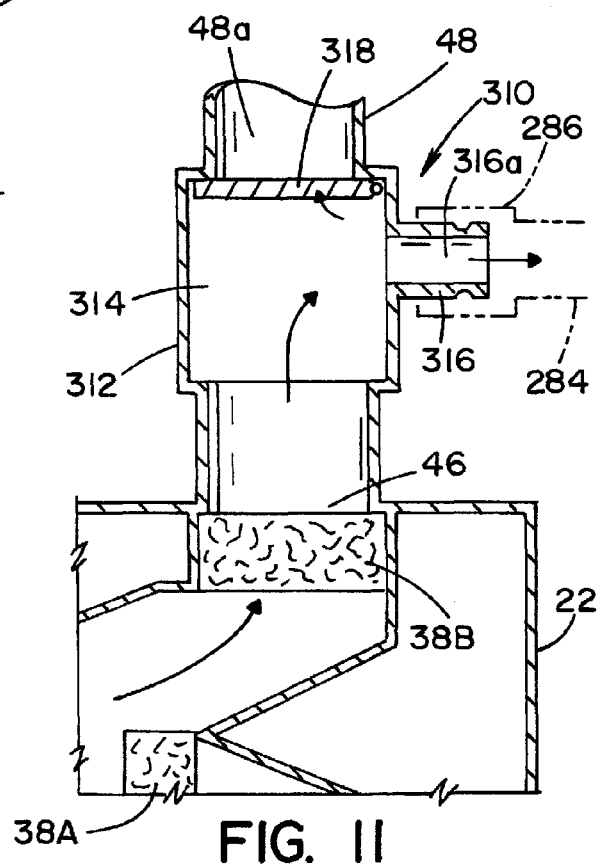

PORTABLE DECONTAMINATION UNIT

RELATED APPLICATIONS

This application claims the benefit of U.S. Provisional Application No. 61/921,586, filed on Dec. 30, 2013, which is fully incorporated herein by reference.

FIELD OF THE INVENTION

The present invention relates generally to decontamination systems, and more particularly to a vapor-phase decontamination system for decontaminating an enclosed region or space.

BACKGROUND OF THE INVENTION

A biosafety cabinet (BSC) is an enclosed, ventilated laboratory workspace that allows laboratory workers to safely work with materials contaminated with (or potentially contaminated with) pathogens. The primary purpose of a biosafety cabinet is to protect laboratory workers and the surrounding environment from pathogens.

The U.S. Centers for Disease Control and Prevention (CDC) classifies biosafety cabinets into three classes. Most biosafety cabinets are a Class II, Type A2 cabinet. The principle of operation of these biosafety cabinets involves using a fan mounted in the top of a cabinet to draw a curtain of sterile air over the materials that are being handled. The air is circulated through a HEPA filter and then directed down underneath a work surface and back up to the top of the cabinet. A certain percentage of the air in the cabinet that is exhausted (after passing through the HEPA filter) is made up by air being drawn into the front of the cabinet underneath the workspace. The air being drawn into the work area acts as a barrier to potentially contaminated air coming back out to the operator. A Class II, Type A2 biosafety cabinet typically recirculates about 70% of the air used therein.

To ensure proper operation, the biosafety cabinet, particularly the HEPA filter, must be periodically cleaned and tested. Prior to servicing the biosafety cabinet, the enclosure must be decontaminated to protect service personnel from exposure to pathogens that may have been collected in the workspace of the cabinet or the filter.

A conventional method of decontaminating biosafety cabinets consists of sealing, i.e., closing, the opening to the workspace, and heating, i.e. boiling, formaldehyde within the enclosure. The formaldehyde vapors decontaminate the exposed surfaces of the workspace. A problem with this method of decontamination is that a residue is produced by the boiling of formaldehyde. The residue must be physically removed from the surfaces of the enclosure by a subsequent cleaning process. Moreover, it is difficult to decontaminate the HEPA filter using a formaldehyde process as described above. In this respect, when formaldehyde is used, a system blower is typically energized for a very short interval to draw some the vaporized formaldehyde into the filter. However, if the blower is allowed to operate too long, the aforementioned residue is collected within the HEPA filter and can clog the filter, thereby requiring its replacement. Too little exposure of the formaldehyde vapor can result in the filter not being completely decontaminated. Moreover, because the blower can be operated for only a relatively short period of time, the enclosure and the air passages downstream of the blower and the HEPA filter are not assuredly decontaminated.

The present invention overcomes this and other problems and provides a method and apparatus for decontaminating an enclosure, particularly a biosafety cabinet, that effectively and efficiently decontaminates the enclosure of a biosafety cabinet as well as the HEPA filter and lower passageways therein.

SUMMARY OF THE INVENTION

In accordance with a preferred embodiment of the present invention, there is provided an apparatus for decontaminating a region within an enclosure. The apparatus comprises a conduit having a passageway therethrough. The passageway defines a path for a carrier gas. The conduit has a first end and a second end, each of the ends being connectable to an enclosure to define a closed-loop path that includes a region defined by the enclosure. A blower is attached to the conduit for re-circulating a carrier gas into, through and out of the region of the enclosure. A nozzle injects a sterilant into the conduit. A space or gap is defined in the conduit. A plurality of tube sections is provided. Each of the tube sections defines a tubular chamber having an opening therethrough and each of the chambers is selectively movable into and out of the gap in the conduit. An opening in a tubular chamber is aligned with the passageway in the conduit when the chamber is disposed in the gap, wherein the opening in the tubular chamber is aligned with the passageway in the conduit. A heating element is disposed in one of the tubular chambers and is operable to heat the carrier gas flowing therethrough. A destroyer is disposed in another of the tubular chambers and is operable to destroy sterilant in the carrier gas. A controller controls movement of the tubular chambers into and out of the gap and the operating of the heating element and the nozzle.

An advantage of the present invention is a system that can decontaminate a biosafety cabinet.

Another advantage of the present invention is a decontamination system that does not require subsequent cleanings of the biosafety cabinet following a decontamination cycle.

A still further advantage of the present invention is a decontamination system as described above that can decontaminate a filter within a biosafety decontamination cabinet without leaving a residue.

Another advantage of the present invention is a decontamination system as described above wherein the entire interior of the biosafety cabinet is exposed to the decontaminant.

A still further advantage of the present invention is a decontamination system as described above that utilizes a recirculation system within a biosafety cabinet to circulate a sterilant through the entire biosafety cabinet.

A still further advantage of the present invention is a decontamination system as described above, wherein the recirculation system within the biosafety cabinet operates continuously during a decontamination cycle.

A still further advantage of the present invention is a decontamination system that utilizes a vaporized sterilant.

A still further advantage of the present invention is a vaporized hydrogen peroxide system that utilizes a solution comprised of 59% hydrogen peroxide and 41% water to create vaporized hydrogen peroxide.

A still further advantage of the present invention is a decontamination system as described above which is portable.

A still further advantage of the present invention is a decontamination system as described above that includes connections for connecting the decontamination system to a biosafety cabinet that fully encloses the workspace of the biosafety cabinet and produces a closed-loop vaporous circulation system.

A still further advantage of the present invention is a compact decontamination system for decontaminating a room or region.

Another advantage of the present invention is a decontamination system as described above that is portable.

A still further advantage of the present invention is a decontamination system as described above that includes a plurality of movable tubular chambers that are each used to perform a phase of a decontamination cycle.

A still further advantage of the present invention is a decontamination system as described above that utilizes a vaporous sterilant.

Another advantage of the present invention is a decontamination system as described above that utilizes vaporous hydrogen peroxide.

A still further advantage of the present invention is a decontamination system as described above having a plurality of tubular passages that are each indexable into a path of a carrier gas.

A still further advantage of the present invention is a decontamination system as described above that has a replaceable canister containing a desiccant.

A still further advantage of the present invention is a decontamination system as described above that is suitable for decontaminating a biosafety cabinet.

A still further advantage of the present invention is a decontamination system as described above that can decontaminate the air circulation system of a biosafety cabinet downstream of the blower.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein:

FIG. 10 is a sectional view of a damper assembly mounted to the exhaust duct of a biosafety cabinet, showing a damper element in an open position allowing a portion of the air that circulates through the biosafety cabinet to be exhausted from the biosafety cabinet;

FIG. 11 is a sectional view of the damper assembly shown in FIG. 10, showing the damper element in a second position wherein a portion of the air circulated through the biosafety cabinet is directed to a exit port.

DETAILED DESCRIPTION OF THE PREFERRED EMBODIMENT

Figure 1:
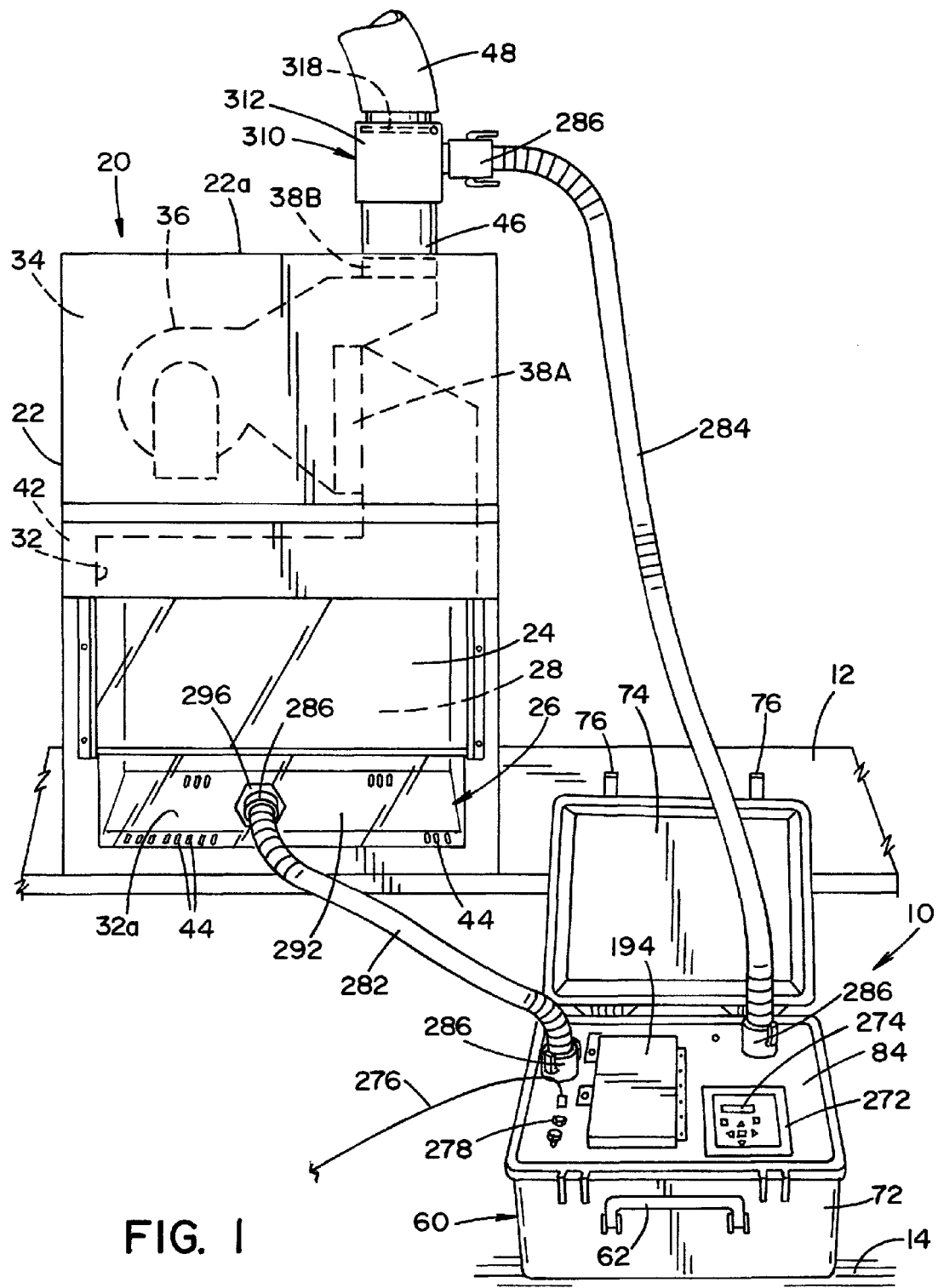
FIG. 1 is a perspective view showing a decontamination system according to the present invention connected to a biosafety cabinet.

Referring now to the drawings wherein the showings are for the purpose of illustrating a preferred embodiment of the invention only and not for the purpose of limiting same, FIG. 1 shows a decontamination system 10, according to a preferred embodiment of the present invention. Decontamination system 10 is particularly applicable in decontaminating a Class II, Type A2 biosafety cabinet, and will be described with particular reference thereto. However, as will be appreciated from a further reading of the present specification, the decontamination system may also find advantageous application in decontaminating other types of biosafety cabinets, as well as decontaminating other types of enclosed regions or spaces.

Figure 12:
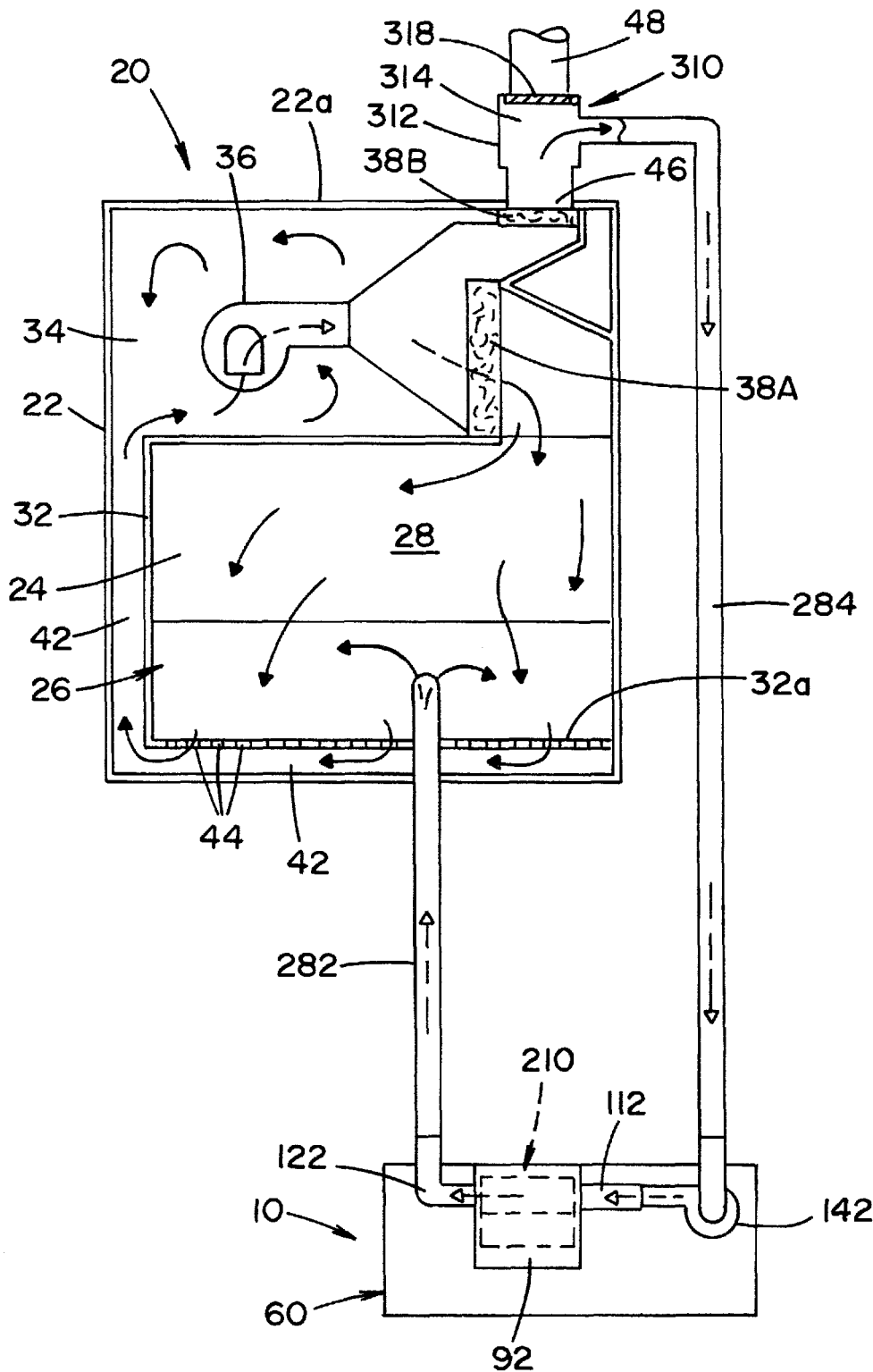
FIG. 12 is a schematic view showing a closed loop circulation system that is established when the decontamination unit is connected to a biosafety cabinet.

In FIG. 1, a Class II, Type A2 biosafety cabinet 20 is shown. Biosafety cabinet 20, in and of itself, forms no part of the present invention. Accordingly, biosafety cabinet 20 shall not be described in great detail. In general, biosafety cabinet 20 is comprised of a rectangular enclosure 22 elevated above the floor 14. In the drawings, biosafety cabinet 20 is shown supported on a table or countertop 12. Enclosure 22 includes a clear front panel 24 having an opening 26 therebelow that provides access to a workspace 28 within biosafety cabinet 20. Workspace 28 is defined by an inner housing 32, best seen in FIG. 12 that is located in a lower portion of rectangular enclosure 22. Inner housing 32 separates workspace 28 from an upper space 34 that contains a blower 36 and HEPA filters 38A and 38B. A duct 42 is defined within biosafety cabinet 20 underneath and around one side of inner housing 32. A bottom wall 32a of inner housing 32 includes slots, or openings 44, that communicate with duct 42. Blower 36 is operable to circulate air throughout enclosure 22, over and in front of workspace 28, as illustrated by the arrows as shown in FIG. 12. An exhaust port 46 is defined in an upper wall 22a of enclosure 22 to allow a portion of the air circulated within biosafety cabinet 20 to be exhausted from biosafety cabinet 20. Exhaust port 46 communicates with an exhaust duct 48. The air exhausted from biosafety cabinet 20 is replaced by air drawn into opening 26 in front panel 24 of biosafety cabinet 20. The air being drawn into workspace 28 acts as a barrier to block potentially contaminated air from escaping out of biosafety cabinet 20, as is conventionally known. Blower 36 is operable to circulate air through biosafety cabinet 20 with a portion of the air inside biosafety cabinet 20 being exhausted and replaced with new air drawn into biosafety cabinet 20, as described above.

Referring now to FIGS. 2-8, decontamination system 10 is best seen. In the embodiment shown, decontamination system 10 is contained within a portable case 60 having a grip or handle 62. Case 60 is comprised of a base portion 72 and a lid portion 74. Base portion 72 defines a generally rectangular cavity that is dimensioned to receive the operative components of decontamination system 10. Lid portion 74 is hinged to base portion 72. Latches 76 on lid portion 74 are provided to securely attach lid portion 74 and base portion 72 together and to allow case 60 to completely enclose decontamination system 10.

Figure 3:
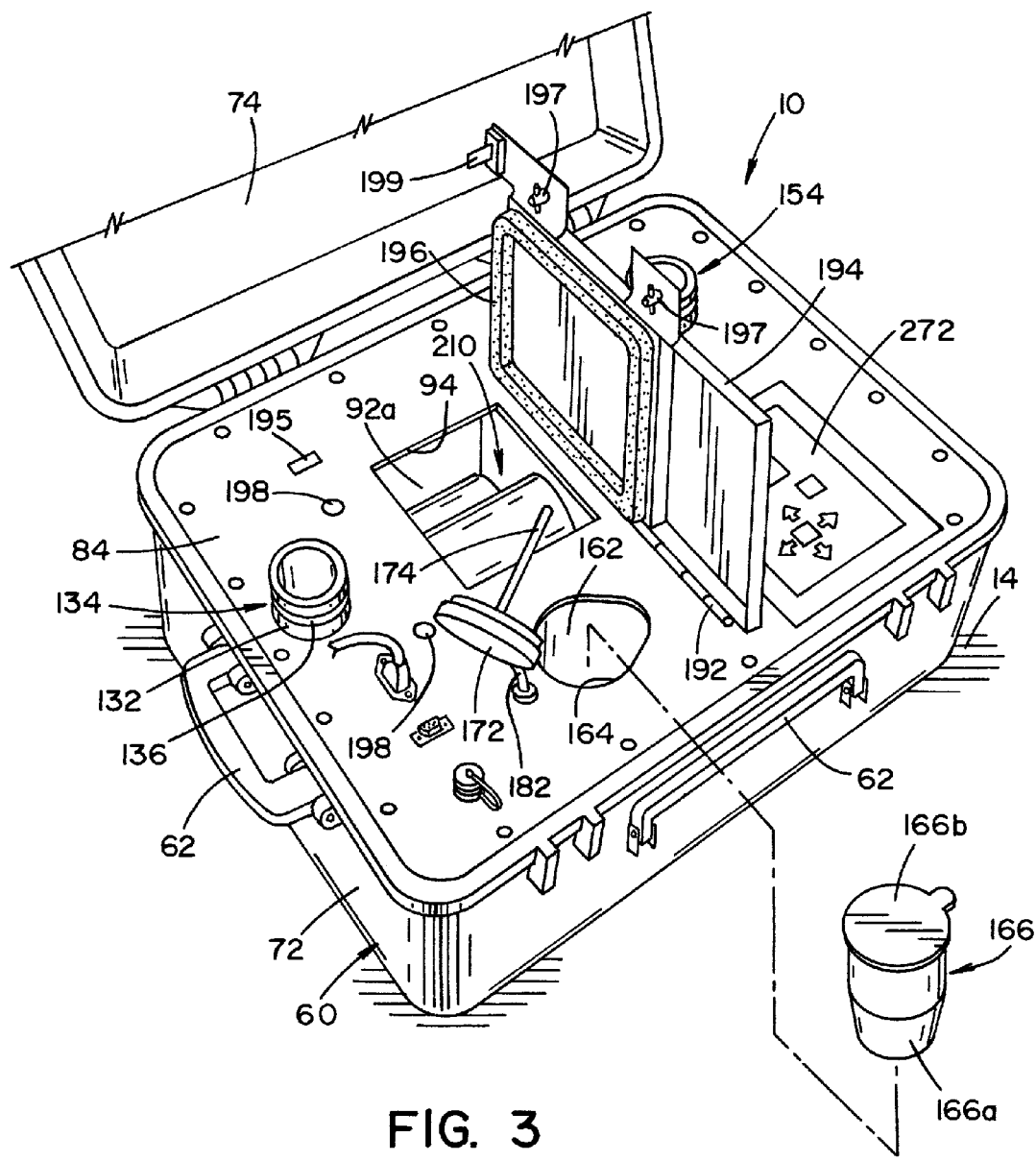
FIG. 3 is a perspective view of the decontamination system shown in FIG. 2 showing a chemical sterilant container removed therefrom.
Figure 4:
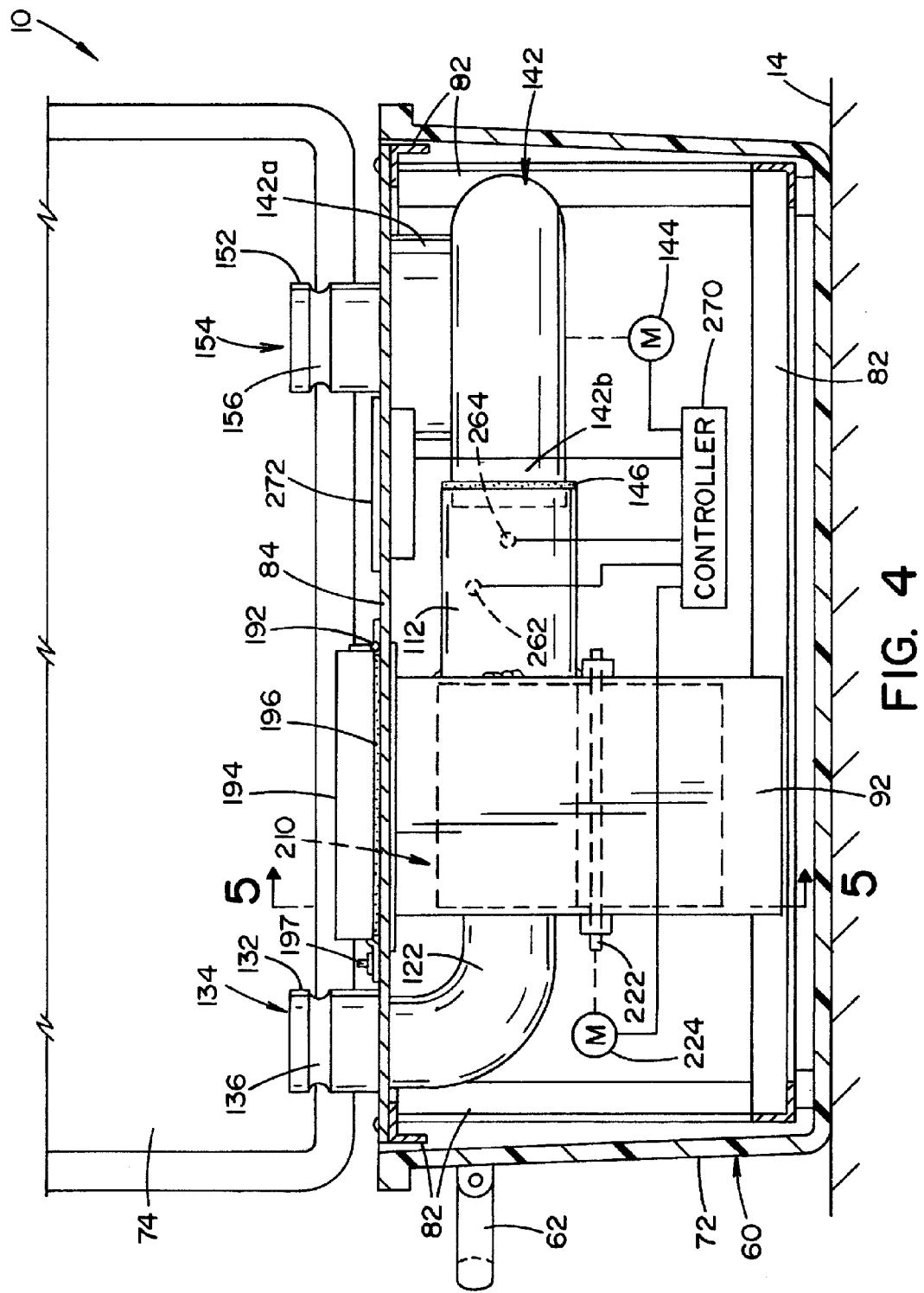
FIG. 4 is a sectional view taken along lines 4-4 of FIG. 2.
Figure 5:
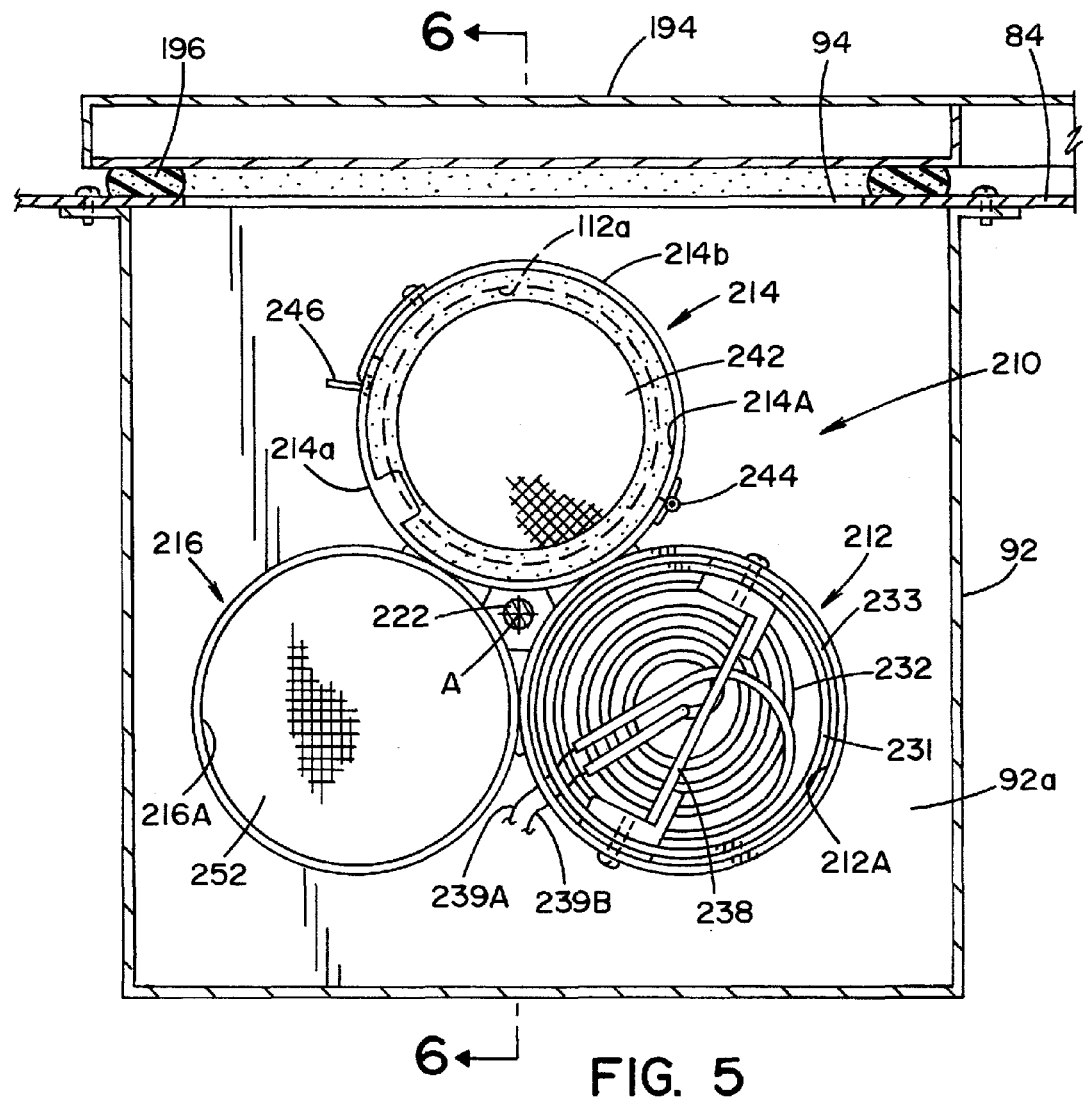
FIG. 5 is a sectional view taken along lines 5-5 of FIG. 4, showing in cross-section three (3) tube sections that form part of a tube assembly.

A frame structure 82, best seen in FIG. 4, is disposed within base portion 72 of case 60. Frame 82 supports a generally flat panel 84. Mounted to flat panel 84, and disposed within base portion 72 of case 60, is a generally rectangular housing 92 that defines an inner chamber 92a. Housing 92 is attached to the underside of flat panel 84 by conventional fasteners, as best seen in FIG. 5. An opening 94 (best seen in FIG. 3), formed through panel 84, communicates with inner chamber 92a of housing 92, to allow access thereto.

In the embodiment shown, housing 92 is generally rectangular in shape. A first tubular member 112 extends from one face of housing 92. A second tubular member 122 extends from an opposing face of housing 92. In the embodiment shown, first tubular member 112 is a straight, cylindrical tube, defining a first passageway 112a. Second tubular member 122 is an L-shaped, cylindrical tube, defining a second passageway 122a. In accordance with one aspect of the present invention, first tubular member 112 is generally aligned with second tubular member 122, such that the first passageway 112a is in alignment with, but spaced from, second passageway 122a. In this respect, a space or gap, defined by chamber 92a of housing 92, exists between first and second tubular members 112, 122.

The free end of L-shaped, second tubular member 122 extends upward through flat panel 84, as best seen in FIG. 4. The free end of second tubular member 122 includes a tubular collar 132 and defines a system outlet 134. Collar 132 has an annular groove 136 formed in the outer surface thereof.

A blower 142 is mounted to the underside of panel 84, adjacent to housing 92. Blower 142 has an inlet 142a connected to a tubular connector 152 extending through panel 84 and defining a system inlet 154. An outlet from blower 142 is connected to the free end of first tubular member 112. A gasket 146 is disposed between outlet 142b of blower 142 and the free end of first tubular member 112.

Figure 6:
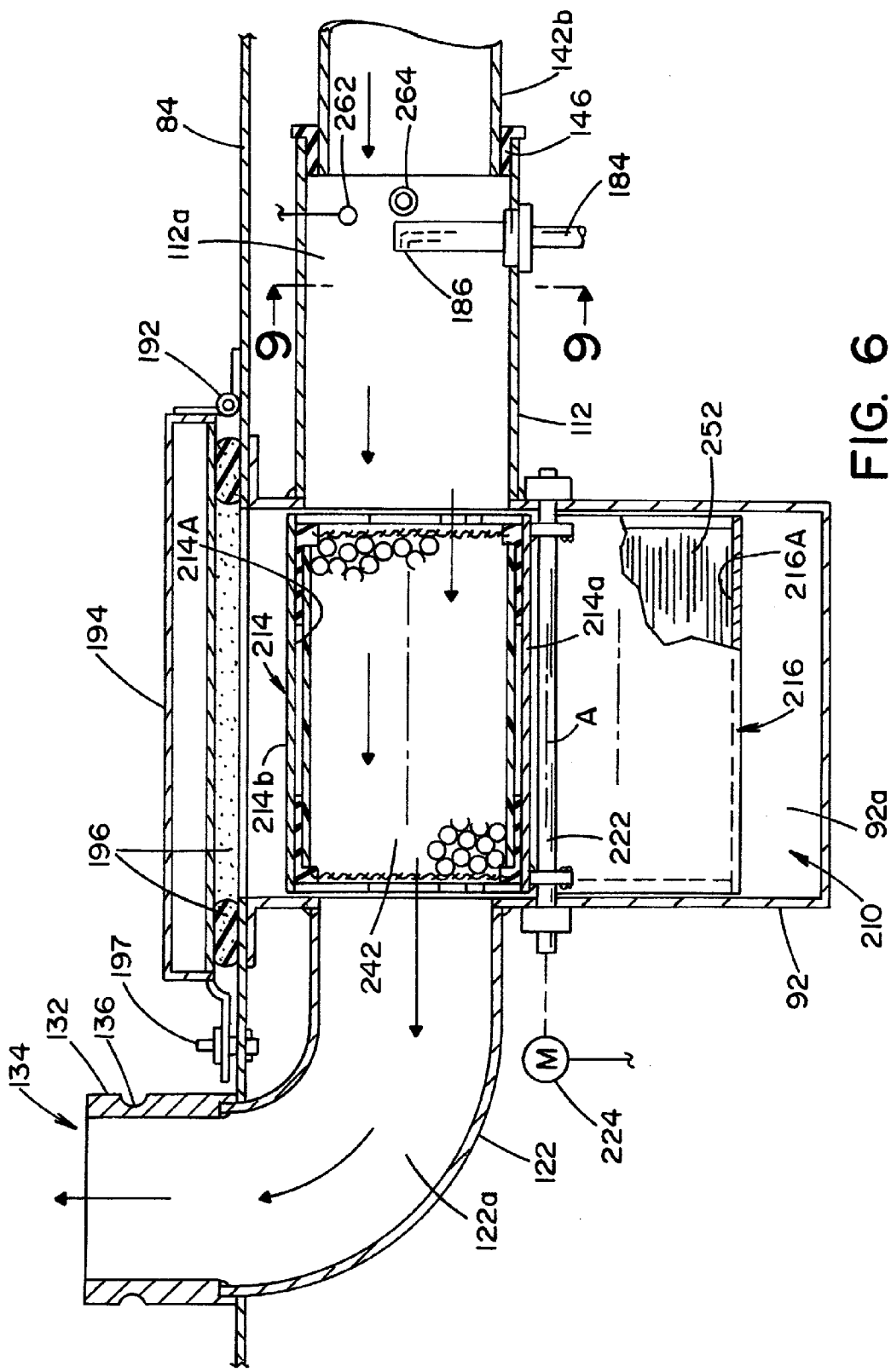
FIG. 6 is a sectional view taken along lines 6-6 of FIG. 5, showing a tube section containing a desiccant canister aligned with a first and second tubular members that form part of a conduit system for conveying a carrier gas to a room or region.

A cup-shaped, reagent receiving well 162 is mounted to the underside of panel 84, adjacent to housing 92. An opening 164 in panel 84 communicates with reagent receiving well 162. Well 162 is dimensioned to receive a closed container 166 containing a liquid sterilant. Container 166 is generally a cup-shaped receptacle 166a, formed preferably of plastic having a foil or mylar layer 166b covering and enclosing container 166a. A cap 172, having a siphoning tube 174 extending therefrom, is dimensioned to be positioned over well 162. Siphoning tube 174 is dimensioned to puncture layer 166b and to extend into sterilant container 166, as shall be described in greater detail below. Flexible tubing 182 is connected to cap 172 and is in fluid communication with siphoning tube 174 extending from cap 172. Tubing 182 is connected to an inlet of a sterilant injection system. The sterilant injection system (not shown) is basically comprised of a pump (not shown) having an outlet tubing 184 connected to an atomizing nozzle 186 disposed within the first passageway of first tubular member 112. Atomizing nozzle 186, best seen in FIG. 6, is supported on an arm extending into first passageway 112a.

Figure 2:
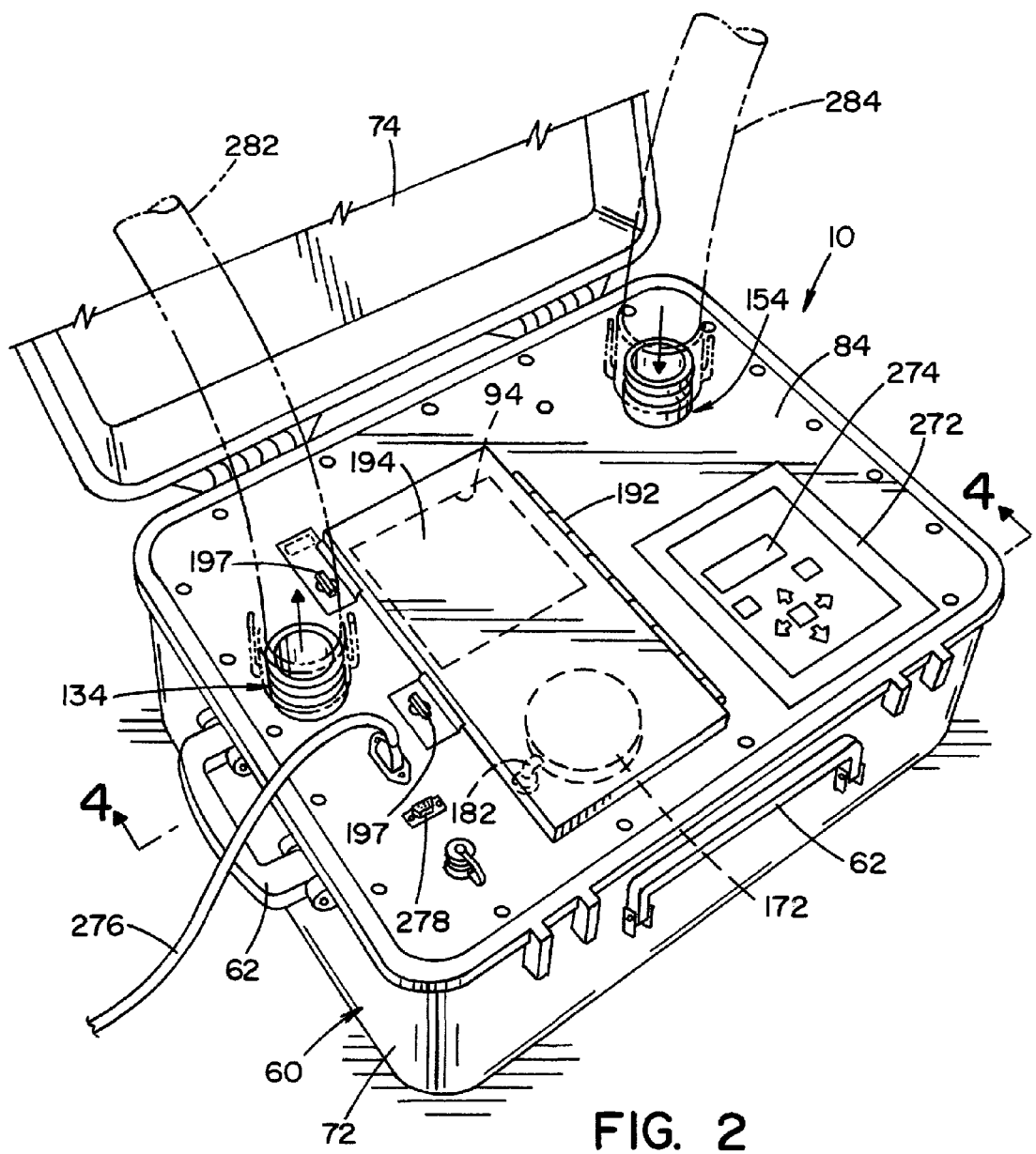
FIG. 2 is an enlarged, top perspective view of the decontamination system, illustrating a preferred embodiment of the present invention.

A hinge 192 connects a cover plate 194 to the upper surface of panel 84. Cover plate 194 is dimensioned to cover opening 94 to chamber 92a and opening 164 to reagent receiving well 162. In this respect, cover plate 194 is movable between a closed position covering openings 94, 164, as shown in FIG. 2, and an opened position allowing access to openings 94, 164, as shown in FIG. 3. A continuous, generally rectangular seal 196 is provided on the underside of cover plate 194 and is dimensioned to surround opening 94 and to form a seal between panel 84 and cover plate 194 when cover plate 194 is in the closed position.

Locking elements 197 on cover plate 194 are provided to be received in openings 198 in panel 84 to lock cover plate 194 in the closed position. A tab 199 on cover plate 194 is dimensioned to be received in a slot 195 in panel 84. A sensor (not shown) on the underside of panel 84 is provided to sense when tab 199 is within slot 195, which indicates that cover plate 194 is in a closed position.

Referring now to FIGS. 5-8, a tube assembly 210, comprised of a plurality of tube sections, is shown. In the embodiment shown, three (3) side-by-side tube sections 212, 214, 216 are shown. Each tube section 212, 214, 216 defines a tubular chamber 212A, 214A, 216A. In the embodiment shown, each tube section is connected to each of the other two (2) tube sections to form a generally triangular configuration when viewed in cross-section, as best seen in FIG. 5. Tube assembly 210 is symmetrical by a central axis "A." A shaft 222 extends along central axis "A" and is connected to each tube section 212, 214, 216. Shaft 222 of tube assembly 210 is mounted to housing 92, such that tube assembly 210 is rotatable about axis "A." Shaft 222 is disposed, i.e., positioned, within housing 92 such that each of the tube sections can be moved, i.e., rotated, into alignment with passageways 112a, 122a defined between the ends of first tubular member 112 and second tubular member 122. When aligned with first and second tubular members 112, 122, a tubular chamber of a tube section essentially completes a path defined by passageways 112a, 122a of first tubular member 112 and second tubular member 122.

One end of shaft 222 is connected to a motor 224 that is schematically illustrated in the drawings. Motor 224 is mounted to outer surface of housing 92. Motor 224 is operable to rotate tube assembly 210 about axis "A," wherein one of tube sections 212, 214, 216 may be aligned with first and second tubular members 112, 122. Each tube section 212, 214, 216 of tube assembly 210 is dimensioned such that each end of a tube section 212, 214, 216 mates closely with the ends of first and second tubular members 112, 122 that communicate with inner chamber 92a of housing 92. When a tube section 212, 214, 216 is aligned with tubular members 112, 122, the aligned tube section is in an "operative position" and a generally continuous path is defined through decontamination system 10. The path extends through first tubular member 112, through an aligned tube section of the tube assembly and continues through to second tubular member 122.

Figure 7:
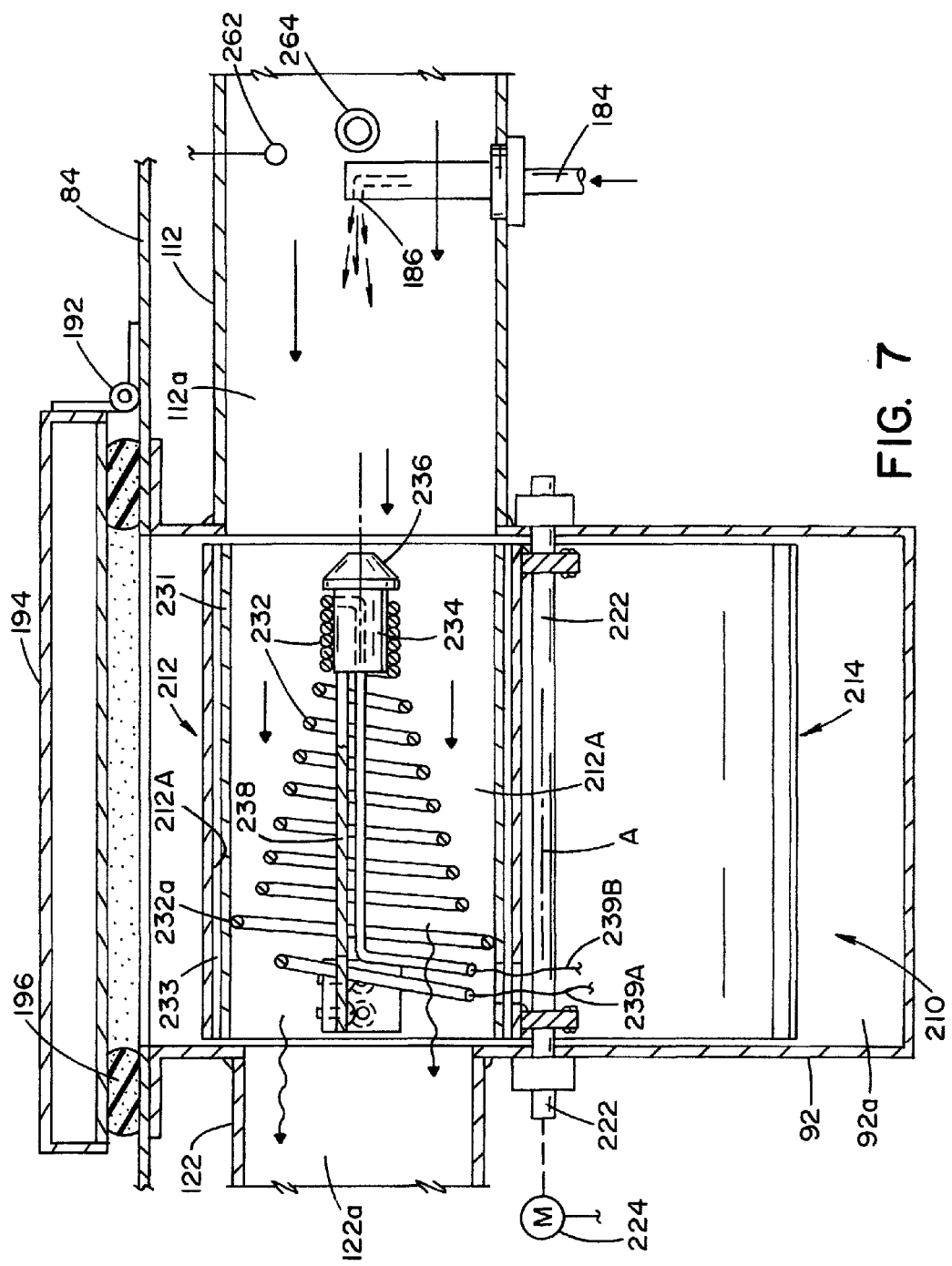
FIG. 7 is a sectional view showing a tube section containing a heating element aligned with the first and second tubular members that form a conduit of the decontamination system.

Tube section 212 of tube assembly 210 contains an atomization tube 231 and a heating element 232. Atomization tube 231 is disposed within tube section 212. Atomization tube 231 is dimensioned such that a gap 233 or space is defined between tube section 212 and atomization tube 231, as best seen in FIG. 7. In the embodiment shown, heating element 232 is coiled into a generally conical shape, best seen in FIG. 7. At least one coil 232a of heating element 232 is in contact with the inner surface of atomization tube 231. The heating element is coiled around a cylindrical pin 234 having a conical end portion 236. Heating element 232 is mounted on a support bracket 238 to be centrally located within tubular chamber 212A of tube section 212, with pin 234 facing blower 142. Electrical leads 239A, 239B extend from heating element 232 through the wall of tube section 212.

Tube section 214 of tube assembly 210 contains a desiccant canister 242. Desiccant canister 242 contains a material that absorbs moisture. The axial ends of canister 242 are perforated to allow air to flow therethrough. According to one aspect of the present invention, tube section 214 is comprised of two tube section halves 214a, 214b. A hinge 244 connects tube section half 214a to half tube section 214b and allows tube 214 to be opened to allow removal and replacement of a desiccant canister 242 therein.

Figure 8:
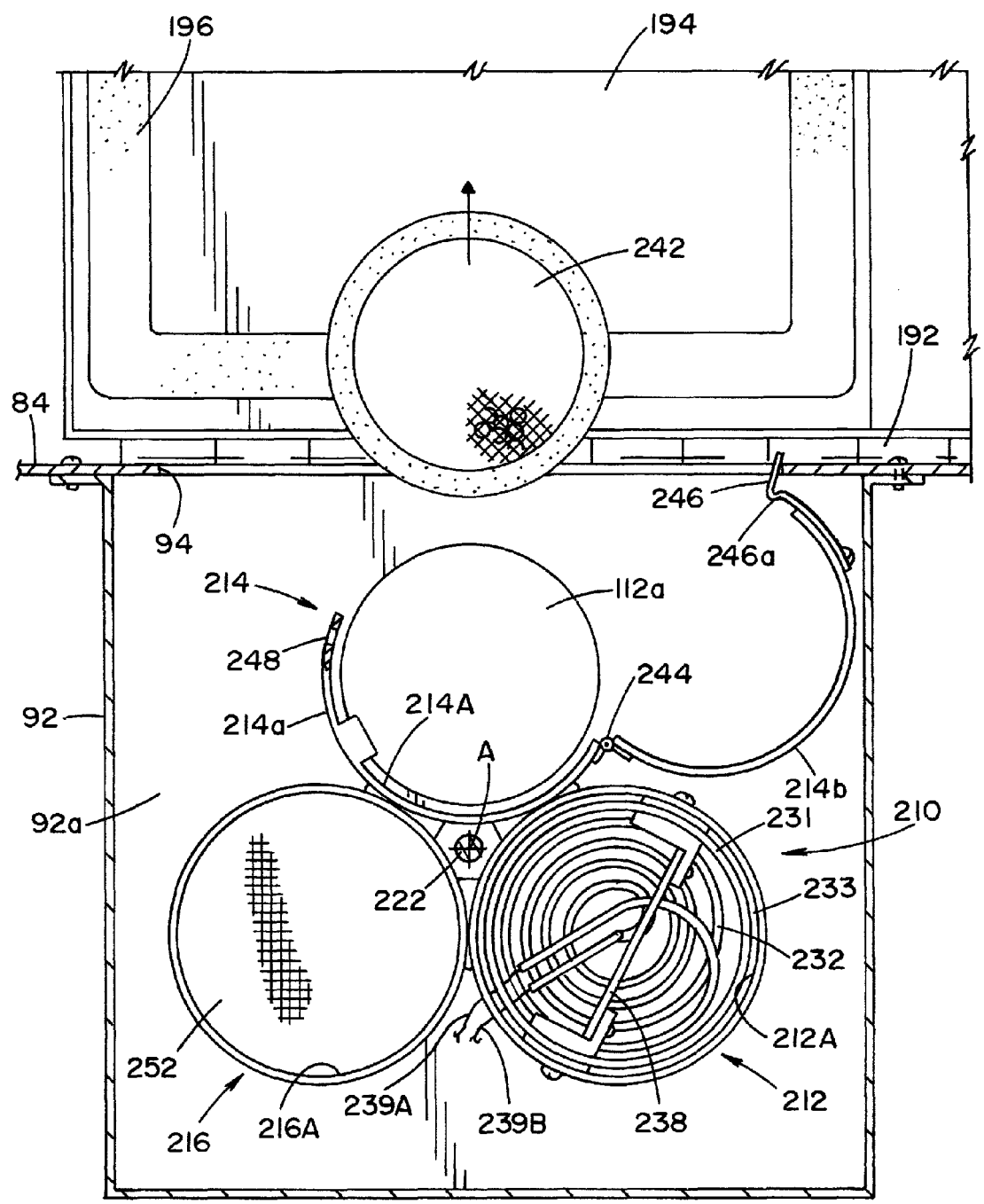
FIG. 8 is a sectional view showing a desiccant canister being removed from one of the tube sections of the tube assembly.
Figure 9:
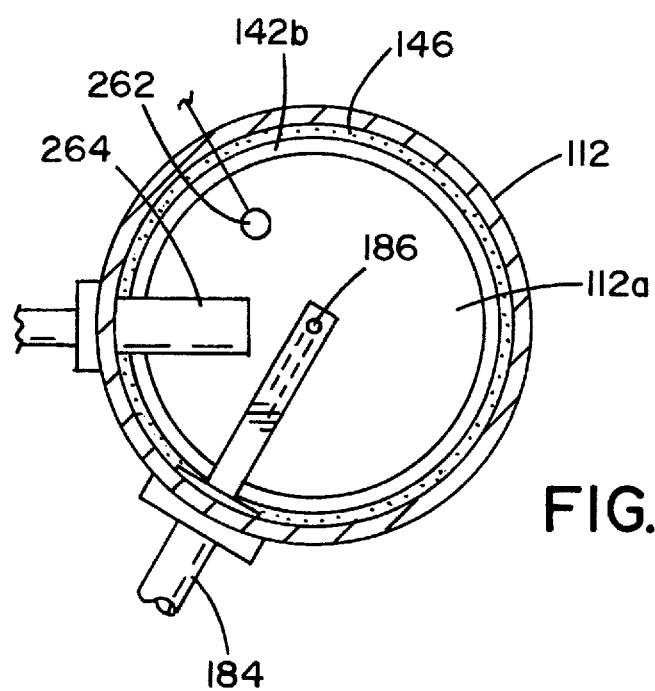
FIG. 9 is a sectional view taken along lines 9-9 of FIG. 6.

A latch element 246, best seen in FIG. 8, is attached to the outer surface of tube section half 214b of tube section 214. Latch element 246 is formed from a strip of resilient material, such as a spring metal, that is formed to have a U-shaped section 246a that defines a tab. U-shaped section 246a is dimensioned to snap lock into a slot 248 formed in tube section half 214a. Latch 246 releasably locks tube section halves 214a, 214b together to secure desiccant canister 242.

As shown in FIG. 8, a desiccant canister 242 can easily be inserted or removed from tube section 214, when tube section 214 is in alignment with first and second tubular members 112, 122, by releasing latch 246 and separating tube section halves 214a, 214b.

Tube section 216 contains a destroyer cartridge 252 therein. Destroyer cartridge 252 contains a material operable to break down a vapor sterilant as the vapor sterilant flows through second tubular chamber 216A. In the embodiment shown, destroyer cartridge 252 is a cylindrical container having perforations formed through the ends thereof to allow axial air flow therethrough.

A temperature sensor 262 and a humidity sensor 264 are disposed within decontamination system 10. Temperature sensor 262 and humidity sensor 264 are preferably disposed within passageway 112a of first tubular member 112.

A controller 270, schematically illustrated in the drawings, is provided within decontamination system 10. Controller 270 is connected to temperature sensor 262 and humidity sensor 264 to receive signals therefrom. Controller 270 is also connected to blower motor 144, motor 224 of tube assembly 210, heating element 232 that is disposed within tube section 212, and sterilant injection pump (not shown) to control the respective operations thereof. A control panel 272 having an interface display 274 is mounted to panel 84 and is connected to controller 270 to allow user input and control. Power to decontamination system 10 is provided by an electrical cable 276 connectable to controller 270 and to an external power source, i.e., a building outlet, (not shown). A serial connection port 278 is provided on panel 84 and is connected to controller 270 to allow external devices to connect to controller 270.

Two (2) flexible hoses 282, 284 are provided to connect decontamination system 10 to biosafety cabinet 20. Each flexible hose includes cylindrical sleeve 286 at the ends thereof. Sleeves 286 are dimensioned to be attached in a tight-fitting relationship to tubular collars 132, 152 on second and first tubular members 122, 112, respectively. One end of first flexible hose 282 is connected to a panel 292 that is attached to biosafety cabinet 20. Panel 292 is dimensioned to cover and enclose opening 26 to biosafety cabinet 20. In this respect, panel 292 is generally rectangular in shape and sized to cover opening 26 to biosafety cabinet 20. Panel 292 is attached to opening 26 of biosafety cabinet 20 by conventional fasteners, tape, or magnetic means (not shown). Panel 292 has a tubular connector 296 extending therefrom, that is dimensioned to receive cylindrical sleeve 286 on the end of first flexible hose 288. Panel 292 is preferably comprised of a polymer material.

Second flexible hose 284 is longer than first hose 282, as best seen in FIG. 1. One end of hose 284 is attached to tubular collar 152 that is connected to blower inlet 142a. The other end of second flexible hose 284 is connected to a tubular connector 316 on a damper assembly 310 that is connected to exhaust duct 48 of biosafety cabinet 20.

Damper assembly 310, best seen in FIGS. 10 and 11, is installed between exhaust port 46 and exhaust duct 48 of biosafety cabinet 20 to control air exhausted therefrom. Damper assembly 310 is generally comprised of a housing 312 defining an inner cavity 314 that communicates with exhaust port 46 and a passageway 48a defined by exhaust duct 48. A tubular connector 316, that is similar in design to tubular collars 132, 152, extends from one side of housing 312. Connector 316 defines an inner passageway 316a that communicates with inner cavity 314 of housing 312. A damper plate 318 is pivotally mounted within housing 312 to be movable between a first position obstructing and covering passageway 316a, as shown in FIG. 10, and a second position, obstructing and covering passageway 48a in exhaust duct 48, as shown in FIG. 11.

Aspects of the present invention shall now be described with reference to the operation of decontamination system 10. Prior to initiating a decontamination cycle, panel 292 is attached to biosafety cabinet 20 to cover access opening 26 to workspace 28. Panel 292 is secured to biosafety cabinet 20 to completely seal opening 26. Hoses 282, 284 are then connected to decontamination system 10 and biosafety cabinet 20, as illustrated in FIG. 1. Damper 318 is moved to its second position, as shown in FIG. 11, to close off exhaust duct 48 and connect the interior of biosafety cabinet 20 to passageway 316a and hose 284.

With the two flexible hoses 282, 284 connecting decontamination system 10 to biosafety cabinet 20 and damper plate 318 in its second position, a closed-loop circulation path is created from decontamination system 10 through first flexible hose 282, though biosafety cabinet 20 and back to decontamination system 10 through second flexible hose 284.

Decontamination system 10 is dimensioned to utilize an enclosed, prepackaged liquid sterilant container 166. A sterilant container 166 is placed into cup-shaped reagent receiving well 162 through opening 164 in flat panel 84 of decontamination system 10. According to another aspect of the present invention, it is contemplated that sterilant container 166 includes an RFID tag, or other means of encoded data, on the side of container 166 that can be read by an RFID reader (not shown) that is connected to controller 270. Encoded information from the RFID tag on sterilant container 166, including the volume of the sterilant enclosed, an expiration date and the like, can be transmitted from the barcode scanner to controller 270 of decontamination system 10 prior to initiating a decontamination cycle.

According to a preferred embodiment of the present invention, decontamination system 10 utilizes a sterilant solution comprised of hydrogen peroxide and water. In a more preferred embodiment, a sterilant solution comprised of 59% hydrogen peroxide by weight and 41% water by weight is used. However, other concentrations of hydrogen peroxide and water are contemplated.

During the operation of decontamination system 10, blower 36 of biosafety cabinet 20 is operated to help the circulation of sterilant throughout biosafety cabinet 20, and particularly, through the HEPA filter 38 and through upper space 34 of biosafety cabinet 20, as shall be described in greater detail below.

Controller 270 is programmed to perform a decontamination cycle that includes: a heating phase; a drying phase; a conditioning phase; a decontamination phase; and an aeration phase. When a decontamination cycle is first initiated, controller 270 causes motor 224 of tube assembly 210 to move tube section 212, that contains heating element 232 into alignment with first and second tubular members 112, 122, as illustrated in FIG. 7. Controller 270 then initiates the "heating phase" by energizing blower motor 144 that cause blower 142 to circulate air (the carrier gas) past heating element 232. The air is conveyed through biosafety cabinet 20 along the closed loop circulation path, as illustrated in FIG. 12. Heating element 232 is energized to heat the air circulated through biosafety cabinet 20 and through decontamination system 10. Temperature sensor 262 within passageway 112a of first tubular member 112 senses the temperature of the air, i.e., the carrier gas, as it is circulated through biosafety cabinet 20 and decontamination system 10.

When the circulated air reaches a desired temperature, about 31° C., heating element 232 is de-energized and motor 224 of tube section assembly 210 is energized to index tube section 214 containing desiccant canister 242 into position in alignment with first and second tubular members 112, 122. With second tube section 214 containing desiccant canister 242 now forming part of the closed loop circulation path, the "drying phase" is initiated. Moisture within the air flowing through biosafety cabinet 20 and decontamination system 10 is removed as the air passes through desiccant canister 242. Humidity sensor 264 within first tubular member 112 monitors the humidity of the air flowing through first tubular member 112 and, thus, provides an indication of the humidity within biosafety cabinet 20. In accordance with the preferred embodiment, the drying phase continues until the air circulating through the closed loop circulation path, i.e., through biosafety cabinet 20, attains a relative humidity of about 15%.

Once a desired humidity level is reached, a "conditioning phase" is initiated. Motor 224 of tube assembly 210 is energized to return tube section 212 containing heating element 232 into position in alignment with first and second tubular members 112, 122. Controller 270 then causes the sterilant injection system, and, more specifically the sterilant pump (not shown), to inject the liquid sterilant from sterilant container 166 to atomizing nozzle 186 within first tubular member 112, thereby creating an atomized mist within first passageway 112a. The air circulating through the closed loop circulation path defined by decontamination system 10 and biosafety cabinet 20 was previously heated and dried during the drying phase. The atomized hydrogen peroxide vaporizes within decontamination system 10. The vaporization process is a hybrid of conventionally known flash vaporization where the liquid hydrogen peroxide is vaporized on a heating plate/element. According to the present invention, the vaporization occurs in several ways. The atomized hydrogen peroxide is introduced into the heated airstream where latent heat is extracted from the airstream to vaporize the hydrogen peroxide. Remaining atomized hydrogen peroxide is flashed vaporized from contact conical end portion 236 and heater element 232. Vaporization is also conducted from contact of the atomized hydrogen peroxide with the inner surface of atomization tube 231 as a result of the transfer of heat from the contact of coil 232a of heating element 232 to the inner surface of atomization tube 231.

The vaporized hydrogen peroxide (VHP) is introduced into the closed-loop circulation path and is conveyed through first flexible hose 282 into work space 28 of biosafety cabinet 20. Since the blower system of biosafety cabinet 20 is operating, the vaporized hydrogen peroxide (VHP) is drawn into upper space 34 where blower 36 in biosafety cabinet 20 circulates 70% of the carrier gas and the vaporized hydrogen peroxide (VHP) contained therein through duct 42 through HEPA filter 38A, to the underside of workspace 28 and back into workspace 28, as illustrated by the arrow in FIG. 12.

30% of the carrier gas and associated vaporized hydrogen peroxide (VHP) is drawn through HEPA filter 38B (exhaust) and through second flexible hose 284 by blower 144 of decontamination system 10 and biosafety cabinet blower 36. In other words, the vaporized hydrogen peroxide (VHP) is introduced into a closed-loop path and is conveyed through flexible hoses 282, 284 by the carrier gas (air) into and back out of biosafety cabinet 20 before it is returned to decontamination system 10. During the conditioning phase, vaporized hydrogen peroxide (VHP) is injected into decontamination system 10 at a relatively high rate to bring the vaporized hydrogen peroxide (VHP) level within biosafety cabinet 20 to a desired level in a short period of time. During the conditioning phase, blower 142 and cabinet blower 36 causes the air within the closed loop path to circulate continuously through first and second flexible hoses 282, 284 and through biosafety cabinet 20. As a result of the continuous circulation of the vaporized hydrogen peroxide (VHP) along the closed-loop path (created by connecting decontamination system 10, first and second flexible hoses 282, 284 and biosafety cabinet 20), the concentration of vaporized hydrogen peroxide (VHP) in biosafety cabinet 20 increases more rapidly than it would if vaporized hydrogen peroxide (VHP) exiting biosafety cabinet 20 was destroyed and exhausted. In other words, the vaporized hydrogen peroxide (VHP) flowing through the closed-loop path continuously circulates through decontamination system 10 and past atomizing nozzle 186 where additional vaporized hydrogen peroxide (VHP) is generated and added to the air stream. The conditioning phase is completed when a predetermined concentration of vaporized hydrogen peroxide has been established within the closed loop system.

After the conditioning phase is completed, the decontamination phase is initiated. During the decontamination phase, the sterilant injection rate to atomizing nozzle 186 is decreased to maintain the concentration of vaporized hydrogen peroxide (VHP) at the desired parts per million (ppm) level. The decontamination phase is run for a predetermined period of time, preferably with the vaporized hydrogen peroxide (VHP) concentration remaining constant, at a level sufficient to effect the desired or decontamination of the interior of biosafety cabinet 20. In this respect, because the blower within biosafety cabinet 20 assists in the circulation of the vaporized hydrogen peroxide (VHP) throughout biosafety cabinet 20 and, more importantly, HEPA filter(s) 38 of biosafety cabinet 20, decontamination of the entire interior of biosafety cabinet 20 is performed. After the decontamination phase is completed, controller 270 causes the pump of the injection system to shut down, thereby shutting off the flow of additional sterilant to atomizing nozzle 186.

Following completion of the decontamination phase, an aeration phase is initiated. At the start of the aeration phase, controller 270 causes tube assembly 210 to rotate tube section 216, containing the destroyer material, into alignment with first and second tubular members 112, 122. Blower motor 144 of decontamination system 10 and blower 36 of biosafety cabinet 20 continue to operate causing the carrier air to continuously circulate along the closed-loop path, wherein the air is forced through and past the destroyer material. Contact with the destroyer material causes the vaporized hydrogen peroxide to break down into water and oxygen. During the aeration phase, blower 142 continues to operate until the vaporized hydrogen peroxide (VHP) level is reduced to an allowable threshold (about 1 ppm).

The present invention provides a compact decontamination system 10 that allows for the decontamination of biosafety cabinets or other similar spaces. By utilizing the circulation system of a biosafety cabinet 20 during the decontamination cycle, the decontamination system 10 can contain a smaller blower, thereby reducing the size, as well as the weight, of decontamination system 10. Still further, tube sections 212, 214, 216 forming tube assembly 210 need not sealingly engage the ends of first and second tubular members 112, 122 when a tube section is indexed in alignment. In this respect, because housing 92 surrounding tube assembly 210 is totally enclosed, any leaks between tube sections 212, 214, 216 and the first and second tubular members 112, 122 is contained within enclosed housing 92. In other words, any vaporized hydrogen peroxide (VHP) generated that may be forced into enclosed housing 92 would be later destroyed during the aeration phase of the decontamination cycle.

The foregoing description is a specific embodiment of the present invention. It should be appreciated that this embodiment is described for purposes of illustration only, and that numerous alterations and modifications may be practiced by those skilled in the art without departing from the spirit and scope of the invention. It is intended that all such modifications and alterations be included insofar as they come within the scope of the invention as claimed or the equivalents thereof.

Having described the invention, the following is claimed:

1. An apparatus for decontaminating a region within an enclosure, said apparatus comprising:
   a conduit having a passageway therethrough, said passageway defining a path for a carrier gas, said conduit having a first end and a second end, each of said ends being connectable to an enclosure to define a closed-loop path that includes a region of said enclosure;
   a blower attached to said conduit for re-circulating a carrier gas into, through and out of said region of said enclosure;
   a nozzle for injecting a sterilant into said conduit;
   a space or gap defined in said conduit;
   a plurality of tubular chambers, each of said chamber having an opening therethrough and each of said chamber being selectively movable into and out of said gap, an opening in a chamber being aligned with said passageway in said conduit when said chamber is disposed in said gap, wherein said opening in said chamber is aligned with said passageway in said conduit;
   a heating element disposed in one of said tubular chambers operable to heat said carrier gas flowing therethrough;
   a destroyer disposed in another of said tubular chambers operable to destroy sterilant in said carrier gas; and
   a controller for controlling movement of said tubular chambers into and out of said gap and the operating of said heating element and said nozzle.

2. An apparatus for decontaminating a region within an enclosure as defined in claim 1, wherein said tubular chambers are disposed about a central axis.

3. An apparatus for decontaminating a region within an enclosure as defined in claim 1, wherein said tubular chambers are disposed side-by-side and rotatable about a central axis.

4. An apparatus for decontaminating a region within an enclosure as defined in claim 1, wherein said apparatus includes three, like tubular chambers disposed side-by-side about a central axis,
   a first of said tubular chambers including a heating element,
   a second of said tubular chambers including a destroying element, and
   a third of said tubular chambers including a desiccant.

5. An apparatus for decontaminating a region within an enclosure as defined in claim 1, wherein a sealed enclosure surrounds said gap in said conduit.

6. An apparatus for decontaminating a region within an enclosure as defined in claim 5, wherein said tubular chambers are contained within said sealed enclosure and are movable therein.

7. An apparatus for decontaminating a region within an enclosure as defined in claim 1, wherein said controller is programmed to perform a decontamination operation for decontaminating said region within said enclosure, said decontamination operation including:
   a heating phase,
   a drying phase,
   a sterilant vaporization phase, and
   a sterilant breakdown phase.

8. An apparatus for decontaminating a region within an enclosure as defined in claim 1, wherein said controller causes a tubular chamber having a heating element to align with said conduit during a carrier gas heating phase.

9. An apparatus for decontaminating a region within an enclosure as defined in claim 1, wherein said controller causes a tubular chamber having a heating element to align with said conduit during a sterilant vaporization phase.

10. An apparatus for decontaminating a region within an enclosure as defined in claim 1, wherein said controller causes a tubular chamber having a desiccant therein to align with said conduit during a drying phase.

11. An apparatus for decontaminating a region within an enclosure as defined in claim 1, wherein said controller causes a tubular chamber having a destroyer therein to align with said conduit during a sterilant breakdown phase.

12. A closed loop, flow through vapor phase decontamination system, comprising:
   a conduit having a passageway therethrough, said passageway defining a path for a carrier gas, said conduit having a first end and a second end, each of said ends being connectable to an enclosure to define a closed-loop path that includes a region of said enclosure;
   a blower connected to said conduit system for re-circulating a carrier gas flow into, through and out of the chamber;
   a nozzle for injecting a sterilant into said closed loop conduit system;
   a destroyer for converting the vaporized hydrogen peroxide in water and oxygen; and
   a heating element operable to heat said carrier gas flowing through said closed loop conduit system,
   wherein said destroyer and said heating element are selectively movable into and out of alignment with said passageway in said conduit, said heating element operable to heat said carrier gas and vaporize said sterilant when said heating element is aligned with said passageway and said destroyer operable to break down said sterilant when said destroyer is aligned with said passageway.

13. A decontamination system as defined in claim 12, wherein said heating element is mounted adjacent to said destroyer, and each is movable along a path into and out of alignment with said passageway through said conduit.

14. A decontamination system as defined in claim 13, wherein said heating element and said destroyer are movable along a circular path.

15. A decontamination system as defined in claim 14, wherein said heating element and said destroyer are each disposed in a tubular chamber and said chambers are rotatable about a central axis.

16. A decontamination system as defined in claim 12, further comprising a desiccant which is selectively movable into and out of alignment with said passageway.

17. A decontamination system as defined in claim 16, wherein said desiccant is mounted adjacent to said heating element and said destroyer and is movable along a path into and out of alignment with said passageway.

18. A decontamination system as defined in claim 17, wherein said heating element, said destroyer, and said desiccant are movable along a circular path.

19. A decontamination system as defined in claim 18, wherein said desiccant is disposed in a tubular chamber that is rotatable about a central axis.

20. A decontamination system as defined in claim 19, wherein said heating element, said destroyer, and said desiccant are movable along a circular path within a sealed enclosure.

* * * * *